US009849113B2

(12) United States Patent
Gil et al.

(10) Patent No.: US 9,849,113 B2
(45) Date of Patent: *Dec. 26, 2017

(54) METHODS OF TREATING α ADRENERGIC MEDIATED CONDITIONS

(71) Applicant: Allergan, Inc., Irvine, CA (US)

(72) Inventors: Daniel W. Gil, Corona del Mar, CA (US); John E. Donello, Dana Point, CA (US); Wenkui K. Fang, Irvine, CA (US); Phong X. Nguyen, Placentia, CA (US); Ken Chow, Newport Coast, CA (US); Todd M. Heidelbaugh, Fountain Valley, CA (US); Dario G. Gomez, Laguna Niguel, CA (US); Michael E. Garst, Newport Beach, CA (US); Santosh C. Sinha, Ladera Ranch, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/446,650

(22) Filed: Mar. 1, 2017

(65) Prior Publication Data
US 2017/0172982 A1    Jun. 22, 2017

Related U.S. Application Data

(63) Continuation of application No. 14/692,042, filed on Apr. 21, 2015, now Pat. No. 9,623,006, which is a continuation of application No. 13/275,029, filed on Oct. 17, 2011, now Pat. No. 9,034,910, which is a continuation-in-part of application No. 12/479,129, filed on Jun. 5, 2009, now Pat. No. 8,071,636.

(60) Provisional application No. 61/059,837, filed on Jun. 9, 2008.

(51) Int. Cl.
*A61K 31/4168*  (2006.01)
*A61K 9/00*  (2006.01)

(52) U.S. Cl.
CPC ........ *A61K 31/4168* (2013.01); *A61K 9/0053* (2013.01)

(58) Field of Classification Search
CPC .......................... A61K 31/4168; A61K 9/0053
See application file for complete search history.

(56) References Cited

U.S. PATENT DOCUMENTS

| | | | |
|---|---|---|---|
| 3,296,077 A | 1/1967 | Berg | A61K 8/4946 424/73 |
| 4,256,755 A | 3/1981 | Smith et al. | |
| 4,665,085 A | 5/1987 | Coquelet | A61K 31/415 514/398 |
| 5,610,184 A | 3/1997 | Shahinian, Jr. | A61K 31/165 514/540 |
| 2003/0022926 A1 | 1/2003 | Lavand'Homme | |
| 2009/0042987 A1 | 2/2009 | Selley | A61K 31/196 514/563 |

FOREIGN PATENT DOCUMENTS

| | | |
|---|---|---|
| EP | 1333028 | 8/2003 |
| FR | 2806082 | 9/2001 |
| GB | 1174988 | 12/1969 |
| WO | 01/78702 | 10/2001 |
| WO | 03-099289 | 12/2003 |
| WO | 2006-012426 | 2/2006 |
| WO | 2008-123821 | 10/2008 |
| WO | 2009-003868 | 1/2009 |
| WO | 2009-052075 | 4/2009 |

OTHER PUBLICATIONS

Boehringer Sohn, C.H., Nouvelles 2-Benzylamino-Imidazolines—(2), Sep. 28, 1967, 4 Pages, FR.
David J. Hart, Preparation of Primary Amines and 2-Azetidinones via N-Trimethylsilyl Imines, J. Org. Chem., Jun. 28, 1982, 289-294, 48, US.
Dixon, W.J., Efficient Analysis of Experimental Observations, Ann. Rev. Pharmacol Toxicol, 1980, 441-462, 20, Annual Reviews Inc.
Joseph, Elizabeth et al., Novel Mechanism of Enhanced Nociception in a Model of AIDS Therapy-Induced Painful Peripheral Neuropathy in the Rat, Pain, 2004, 147-158, 107.
Kim, Sun et al., An experimental model for peripheral neuropathy produced by segmental spinal nerve ligation in the rat, Pain 1992, 150: 353-363.
Kosasayama, Akira et al., Cyclic Guanidines VII. Structure-Activity Relationships of Hypoglycemic Cyclic Guanidines, Chemical and Pharmaceutical Bulletin, 1979, 1596-1603, 27 (7), US.
Kostric, V. et al., Midbrain Dopaminergic Neuronal Degeneration in a Transgenic Mouse Model of Familial Amyotrophic Lateral Sclerosis, Ann Neurol, 1997, 497-904, 41.
Mann, D.M.A. et al., Dopaminergic Neurotransmitter Systems in Alzheimer's Disease and in Down's Syndrome at Middle Age, Journal of Neurology, 1987, 341-344, 50.
Messier, Terri, High Throughput Assays of Cloned Adrenergic, Muscarinic, Neurokinin, and Neurotrophin Receptors in Living Mammalian Cells, Pharmacology & Toxicology, 1995, 308-311, 76, US.
Perez-Tomas, Ricardo, Multidrug Resistance: Retrospect and Prospects in Anti-Cancer Drug Treatment, Current Medicinal Chemistry, 2006, 1859-1876, 13.

(Continued)

*Primary Examiner* — Sarah Pihonak
(74) *Attorney, Agent, or Firm* — Barbara C. Potts

(57) ABSTRACT

Described herein are compounds for and methods of treating conditions or diseases in a subject by administering to the subject a pharmaceutical composition containing an effective amount of an α-adrenergic modulator. The compounds and methods are also useful for alleviating types of pain, acute, neuropathic and chronic.

5 Claims, 3 Drawing Sheets

(56) References Cited

OTHER PUBLICATIONS

Saczewski, F., Synthesis, Structure, and Binding of Some 2-Imidazolines to Rat Brain Alfa-1 and Alfa-2-Adrenergic Receptors, Arch. Pharm. Pharm. Med. Chem, 2000, 425-430, 333, US.
Silverman, Richard B., Prodrugs and Delivery Systems (Chapter 8), The Organic Chemistry of Drug Delivery and Drug Design and Drug Action Second Edition, 2004, 496-557.
Summers, Roger, Displacement of 3H Clonidine Binding by Clonidine Analogues in Membranes from Rat Cerebral Cortex, European Journal of Pharmacology, 1980, 233-241, 66, US.
Zarkovic, Kamelija, 4-Hydroxynonenal and Neurodegenerative Diseases, Molecular Aspects of Medicine, 2003, 293-303, 24.
International Search Report, Form PCT-ISA-220, PCT/US2009/046436, 15 Pages, Jul. 23, 2009.
International Search Report, Form PCT-ISA-220, PCT/US2009/046432, 17 Pages, Jul. 24, 2009.

METHODS OF TREATING α ADRENERGIC MEDIATED CONDITIONS

CROSS-REFERENCE TO RELATED APPLICATION

This application is a continuation of U.S. patent application Ser. No. 14/692,042 filed on Apr. 21, 2015, which is a continuation of U.S. patent application Ser. No. 13/275,029, filed on Oct. 17, 2011, which issued as U.S. Pat. No. 9,034,910 on May 19, 2015, which is a continuation-in-part of U.S. patent application Ser. No. 12/479,129, filed on Jun. 5, 2009, which issued as U.S. Pat. No. 8,071,636 on Dec. 6, 2011, and which claims priority under 35 U.S.C. §120 to U.S. Provisional Patent Application No. 61/059,837 filed on Jun. 9, 2008, each of which is incorporated herein by reference.

FIELD OF THE INVENTION

The present invention relates to methods of using compounds as disclosed herein to treat pain.

BACKGROUND OF THE INVENTION

Clinical pain encompasses nociceptive and neuropathic pain. Each type of pain is characterized by hypersensitivity at the site of damage and in adjacent normal tissue. While nociceptive pain usually is limited in duration and responds well to available opioid therapy, neuropathic pain can persist long after the initiating event has healed, as is evident, for example, in the "ghost pain" that often follows amputation. Chronic pain syndromes such as chronic neuropathic pain are triggered by any of a variety of insults, including surgery, compression injury or trauma, infectious agent, toxic drug, inflammatory disorder, or a metabolic disease such as diabetes or ischemia.

Neuropathic pain is a unique kind of chronic pain that is distinct from acute pain or inflammatory pain. Neuropathic pain, in contrast to most types of pain, persists in the absence of any detectable, on-going tissue injury process. It is common in patients that experience nerve injury in conditions such as diabetic neuropathy, post-herpetic neuralgia and chemotherapy-induced neuritis. A common feature is the occurrence of allodynia, which is defined as the perception of normally innocuous stimuli as being painful.

Unfortunately, chronic pain such as chronic neuropathic pain generally is resistant to available drug therapy. Furthermore, current therapies have serious side-effects such as cognitive changes, sedation, nausea and, in the case of narcotic drugs, addiction. Many patients suffering from neuropathic and other chronic pain are elderly or have medical conditions that limit their tolerance to the side-effects associated with available analgesic therapy. The inadequacy of current therapy in relieving neuropathic pain without producing intolerable side-effects often is manifest in the depression and suicidal tendency of chronic pain sufferers.

As alternatives to current analgesics, $\alpha_2$ adrenergic agonists, which are devoid of respiratory depressant effects and addictive potential are being developed. Such drugs are useful analgesic agents when administered spinally. However, undesirable pharmacological properties of α-adrenergic agonists, specifically sedation and hypotension, limit the utility of these drugs when administered orally or by other peripheral routes. Thus, there is a need for effective analgesic agents that can be administered by oral or other peripheral routes and that lack undesirable side-effects such as sedation and hypotension. The present invention satisfies this need and provides related advantages as well.

Also provided herein are new therapies for chronic pain sufferers, who, until now, have faced a lifetime of daily medication to control their pain. Unfortunately, available treatments for chronic neuropathic pain, such as tricyclic antidepressants, anti-seizure drugs and local anesthetic injections, only alleviate symptoms temporarily and to varying degrees. No available treatment reverses the sensitized pain state or cures pain such as neuropathic pain. Effective drugs that can be administered, for example, once or several times a month and that maintain analgesic activity for several weeks or months, are presently not available. Thus, there is a need for novel methods of providing long-term relief from chronic pain. The present invention satisfies this need and also provides related advantages.

SUMMARY OF THE INVENTION

Described herein are compounds for and methods of treating conditions or diseases in a subject by administering to the subject a pharmaceutical composition containing an effective amount of an α-adrenergic modulator. The compounds and methods are also useful for alleviating types of pain, acute, neuropathic and chronic.

Described herein is a method of treating a condition or disease alleviated by activation of α-adrenergic receptors in a mammal comprising: administering a compound having a structure

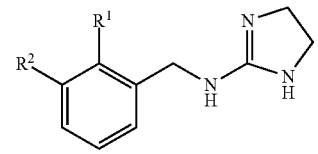

wherein $R^1$ and $R^2$ are each independently selected from hydrogen, $C_{1-4}$ alkyl, $C_{1-4}$ alkoxy, OH, halogen, $NR'_2$, CN, $CO_2R'$, $C(O)NR'R''$, alcohol, $C_{1-4}$ halogenated alkyl, $C_{1-4}$ halogenated alkoxy, and substituted or unsubstituted aryl or heteroaryl; R' is selected from hydrogen, $C_{1-4}$ alkyl and $C_{1-4}$ halogenated alkyl, substituted or unsubstituted aryl or heteroaryl; R" is selected from hydrogen and $C_{1-4}$ alkyl, substituted or unsubstituted aryl or heteroaryl; and wherein the compound activates at least one of the α-adrenergic receptors.

Also described herein is a composition for treating a condition or disease alleviated by activation of α-adrenergic receptors in a mammal comprising: a compound having a structure

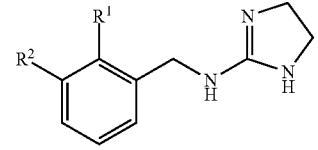

wherein $R^1$ and $R^2$ are each independently selected from hydrogen, $C_{1-4}$ alkyl, $C_{1-4}$ alkoxy, OH, halogen, $NR'_2$, CN, $CO_2R'$, $C(O)NR'R''$, alcohol, $C_{1-4}$ halogenated alkyl, $C_{1-4}$ halogenated alkoxy, and substituted or unsubstituted aryl or heteroaryl; R' is selected from hydrogen, $C_{1-4}$ alkyl and $C_{1-4}$ halogenated alkyl, substituted or unsubstituted aryl or heteroaryl; R" is selected from hydrogen and $C_{1-4}$ alkyl, substituted or unsubstituted aryl or heteroaryl; and wherein the compound activates at least one of the α-adrenergic receptors.

In one embodiment, the condition or disease is selected from the group consisting of hypertension, congestive heart failure, asthma, depression, glaucoma, elevated intraocular pressure, ischemic neuropathies, optic neuropathy, pain, visceral pain, corneal pain, headache pain, migraine, cancer pain, back pain, irritable bowel syndrome pain, muscle pain, pain associated with diabetic neuropathy, the treatment of diabetic retinopathy, other retinal degenerative conditions, stroke, cognitive deficits, neuropsychiatric conditions, drug dependence, drug addiction, withdrawal symptoms, obsessive compulsive disorder, obesity, insulin resistance, stress related conditions, diarrhea, diuresis, nasal congestions, spasticity, attention deficit disorder, psychoses, anxiety, autoimmune disease, Crohn's disease, gastritis, Alzheimer's disease, Parkinson's disease, amyotrophic lateral sclerosis, and other neurodegenerative diseases. In one embodiment, the condition or disease is pain.

In another embodiment the condition or disease is selected from the group consisting of postherpetic neuralgia (PHN), post-traumatic neuropathy pain (PTN), complex regional pain syndrome (CRPS) and drug-induced neuropathy.

In one embodiment, $R^1$ and $R^2$ are each independently a halogen or halogenated alkyl. In another embodiment, the compound is N-(2-chloro-3-fluoro-benzyl)-4,5-dihydro-1H-imidazol-2-amine. In another embodiment, the compound is N-(2-difluoromethoxy-benzyl)-4,5-dihydro-1H-imidazol-2-amine. In another embodiment, the compound is N-(2,3-dimethyl-benzyl)-4,5-dihydro-1H-imidazol-2-amine. In another embodiment, the compound is N-(trifluoromethyl-benzyl)-4,5-dihydro-1H-imidazol-2-amine. In another embodiment, the compound is N-(trifluoromethoxy-benzyl)-4,5-dihydro-1H-imidazol-2-amine. In another embodiment, the compound is N-(2-fluoro-benzyl)-4,5-dihydro-1H-imidazol-2-amine. In another embodiment, the compound is N-(2-fluoro-3-trifluoromethyl-benzyl)-4,5-dihydro-1H-imidazol-2-amine. In another embodiment, the compound is N-(2,3-dimethoxy-benzyl)-4,5-dihydro-1H-imidazol-2-amine. In another embodiment, the compound is N-(3-bromo-2-methoxy-benzyl)-4,5-dihydro-1H-imidazol-2-amine. In another embodiment, the compound is N-(2-chloro-benzyl)-4,5-dihydro-1H-imidazol-2-amine. In another embodiment, the compound is N-(2-methyl-benzyl)-4,5-dihydro-1H-imidazol-2-amine. In another embodiment, the compound is N-(3-chloro-2-fluoro-benzyl)-4,5-dihydro-1H-imidazol-2-amine. In another embodiment, the compound is N-(2,3-dichlorobenzyl)-4,5-dihydro-1H-imidazol-2-amine. In another embodiment, the compound is N-(2,3-dimethylbenzyl)-4,5-dihydro-1H-imidazol-2-amine. In another embodiment, the compound is N-(2-fluorobenzyl)-4,5-dihydro-1H-imidazol-2-amine.

In one embodiment, the compound is selected from the group consisting of N-(2-chloro-3-fluoro-benzyl)-4,5-dihydro-1H-imidazol-2-amine, N-(2-difluoromethoxy-benzyl)-4,5-dihydro-1H-imidazol-2-amine, N-(2,3-dimethyl-benzyl)-4,5-dihydro-1H-imidazol-2-amine, N-(trifluoromethyl-benzyl)-4,5-dihydro-1H-imidazol-2-amine, N-(trifluoromethoxy-benzyl)-4,5-dihydro-1H-imidazol-2-amine, N-(2-fluoro-benzyl)-4,5-dihydro-1H-imidazol-2-amine, N-(2-fluoro-3-trifluoromethyl-benzyl)-4,5-dihydro-1H-imidazol-2-amine, N-(2,3-dimethoxy-benzyl)-4,5-dihydro-1H-imidazol-2-amine, N-(3-bromo-2-methoxy-benzyl)-4,5-dihydro-1H-imidazol-2-amine, N-(2-chloro-benzyl)-4,5-dihydro-1H-imidazol-2-amine, N-(2-methyl-benzyl)-4,5-dihydro-1H-imidazol-2-amine, N-(3-chloro-2-fluoro-benzyl)-4,5-dihydro-1H-imidazol-2-amine, N-(2,3-dichlorobenzyl)-4,5-dihydro-1H-imidazol-2-amine, N-(2,3-dimethylbenzyl)-4,5-dihydro-1H-imidazol-2-amine, N-(2-fluorobenzyl)-4,5-dihydro-1H-imidazol-2-amine, and combinations thereof.

DEFINITION OF TERMS

Figure 1:
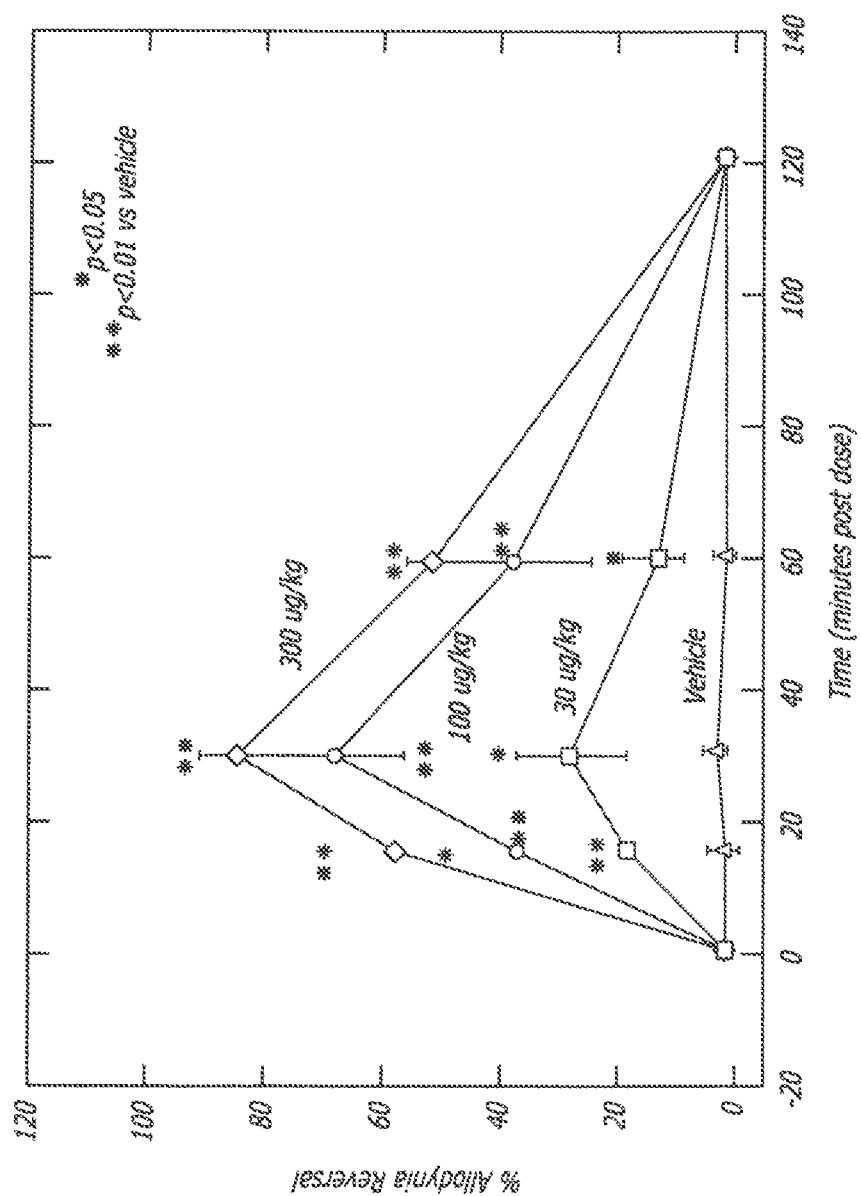
FIG. 1 depicts the peripheral analgesic effects of a single oral dose of N-(2,3-dichlorobenzyl)-4,5-dihydro-1H-imidazol-2-amine in Chung model rats at 30 μg/kg, 100 μg/kg or 300 μg/kg.

Prodrug: A "prodrug" is a compound which is converted to a therapeutically active compound after administration. While not intending to limit the scope, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

Halogen: As used herein, "halogen" is used to refer to a substituent found in column VIIA of the periodic table of elements, including fluorine, chlorine, bromine, and iodine.

Tautomer: As used herein, "tautomer" refers to the migration of protons between adjacent single and double bonds. The tautomerization process is reversible. Compounds described herein can undergo the following tautomerization:

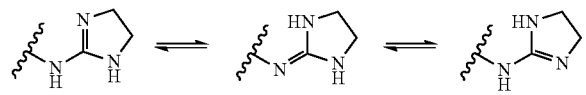

DETAILED DESCRIPTION OF THE INVENTION

Described herein are N-(2 and/or 3-substituted benzyl)-4,5-dihydro-1H-imidazol-2-amine compounds as subtype selective $α_{2A}$ and/or $α_{2C}$ adrenergic modulators having the general structure

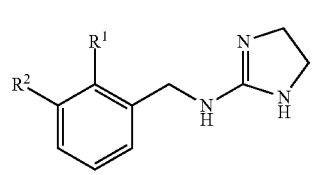

Formula 1 wherein $R^1$ and $R^2$ are each independently selected from hydrogen, $C_{1-4}$ alkyl, $C_{1-4}$ alkoxy, OH, halogen, $NR'_2$, CN, $CO_2R'$, $C(O)NR'R''$, alcohol, $C_{1-4}$ halogenated alkyl, $C_{1-4}$ halogenated alkoxy, and substituted or unsubstituted aryl or heteroaryl; R' is selected from hydrogen, $C_{1-4}$ alkyl and $C_{1-4}$ halogenated alkyl, substituted or unsubstituted aryl or heteroaryl; and R" is selected from hydrogen and $C_{1-4}$ alkyl, substituted or unsubstituted aryl or heteroaryl.

In one embodiment, wherein $R^1$ and $R^2$ are each independently selected from hydrogen, $C_{1-10}$ alkyl, $C_{1-10}$ alkoxy, OH, halogen, $NR'_2$, CN, $CO_2R'$, $C(O)NR'R''$, alcohol, $C_{1-10}$ halogenated alkyl, $C_{1-10}$ halogenated alkoxy, and substituted or unsubstituted aryl or heteroaryl; R' is selected from hydrogen, $C_{1-10}$ alkyl and $C_{1-10}$ halogenated alkyl, substituted or unsubstituted aryl or heteroaryl; and R" is selected from hydrogen and $C_{1-10}$ alkyl, substituted or unsubstituted aryl or heteroaryl.

$R^1$ and $R^2$ can each independently be a $C_{1-10}$ alkyl, which includes $C_{3-10}$ cycloalkyls and $C_{3-10}$ branched alkyls. $R^1$ and $R^2$ can each also independently be a substituted or unsubstituted aryl or heteroaryl which can include aromatic, heteroaromatic, or multi-heteroaromatic groups. The substituted or unsubstituted aryl or heteroaryl can be selected from phenyl, pyridinyl, thienyl, furyl, naphthyl, quinolinyl, indanyl or benzofuryl. Exemplary substituted or unsubstituted aryls or heteroaryls include, but are not limited to, benzenes, pyridines, thiophenes, furans, naphthalenes, quinolines, indans and benzofurans. The aryl groups may be substituted with any common organic fictional group. Such aryl groups may be bonded to Formula 1 at any available position on the aryl group.

An exemplary aryl group is a benzene (Formula 2):

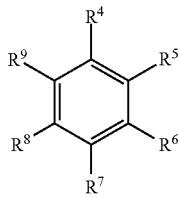

Formula 2 wherein at least one of $R^{4-9}$ must be Formula 1 and wherein the remaining $R^{4-9}$ may be each independently substituted with a common organic functional group including, but not limited to, hydrogen, a $C_{1-10}$ alkyl, $C_{1-10}$ alkenyl, $C_{1-10}$ alkynyl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynyl, aryl, halogen, hydroxyl, alkoxy, amino, cyano, nitro, or thiol group.

Another aryl group may be a pyridine as in Formula 3:

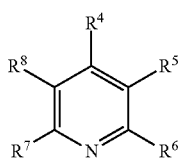

Formula 3 wherein at least one of $R^{4-8}$ must be Formula 1 and wherein the remaining $R^{4-8}$ may be each independently substituted with a common organic functional group including, but not limited to, hydrogen, a $C_{1-10}$ alkyl, $C_{1-10}$ alkenyl, $C_{1-10}$ alkynyl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynyl, aryl, halogen, hydroxyl, alkoxy, amino, cyano, nitro, or thiol group.

Another aryl group may be a thiophene as in Formula 4:

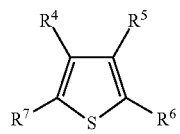

Formula 4 wherein at least one of $R^{4-7}$ must be Formula 1 and wherein the remaining $R^{4-7}$ may be each independently substituted with a common organic functional group including, but not limited to, hydrogen, a $C_{1-10}$ alkyl, $C_{1-10}$ alkenyl, $C_{1-10}$ alkynyl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynyl, aryl, halogen, hydroxyl, alkoxy, amino, cyano, nitro, or thiol group.

Another aryl group may be a furan as in Formula 5:

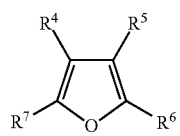

Formula 5 wherein at least one of $R^{4-7}$ must be Formula 1 and wherein the remaining $R^{4-7}$ may be each independently substituted with a common organic functional group including, but not limited to, hydrogen, a $C_{1-10}$ alkyl, $C_{1-10}$ alkenyl, $C_{1-10}$ alkynyl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynyl, aryl, halogen, hydroxyl, alkoxy, amino, cyano, nitro, or thiol group.

Another aryl group may be a naphthalene as in Formula 6:

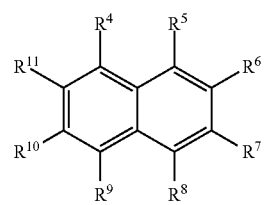

Formula 6 wherein at least one of $R^{4-11}$ must be Formula 1 and wherein the remaining $R^{4-11}$ may be each independently substituted with a common organic functional group including, but not limited to, hydrogen, a $C_{1-10}$ alkyl, $C_{1-10}$ alkenyl, $C_{1-10}$ alkynyl, aryl, halogen, hydroxyl, alkoxy, amino, cyano, nitro, thiol, or carboxy group substituted with a $C_{1-10}$ alkyl, $C_{1-10}$ alkenyl. $C_{1-10}$ alkynyl, aryl, halogen, hydroxyl, alkoxy, amino, cyano, nitro, or thiol group.

Another aryl group may be a quinoline as in Formula 7:

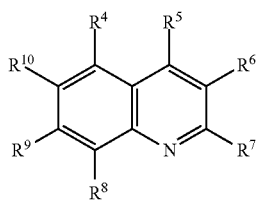

Formula 7 wherein at least one of $R^{4-10}$ must be Formula 1 and wherein the remaining $R^{4-10}$ may be each independently substituted with a common organic functional group including, but not limited to, hydrogen, a $C_{1-10}$ alkyl, $C_{1-10}$ alkenyl, $C_{1-10}$ alkynyl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynyl, aryl, halogen, hydroxyl, alkoxy, amino, cyano, nitro, or thiol group.

Another aryl group may be an indene as in Formula 8:

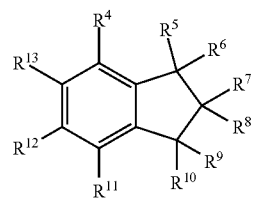

Formula 8 wherein at least one of $R^{4-13}$ must be Formula 1 and wherein the remaining $R^{4-13}$ may be each independently substituted with a common organic functional group including, but not limited to, hydrogen, a $C_{1-10}$ alkyl, $C_{1-10}$ alkenyl, $C_{1-10}$ alkynyl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynyl, aryl, halogen, hydroxyl, alkoxy, amino, cyano, nitro, or thiol group.

Another aryl group may be a benzofuran as in Formula 9:

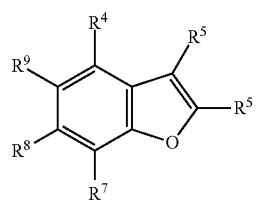

Formula 9 wherein at least one of $R^{4-9}$ must be Formula 1 and wherein the remaining $R^{4-9}$ may be each independently substituted with a common organic functional group including, but not limited to, hydrogen, a $C_{1-10}$ alkyl, $C_{1-10}$ alkenyl, $C_{1-10}$ alkynyl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynyl, aryl, halogen, hydroxyl, alkoxy, amino, cyano, nitro, or thiol group.

$\alpha_2$ adrenergic receptors have been characterized by molecular and pharmaceutical methods; the methods including $\alpha_{1A}$, $\alpha_{1B}$, $\alpha_{1D}$, $\alpha_{2A}$, $\alpha_{2B}$ and $\alpha_{2C}$ subtypes. Activation of these $\alpha$-receptors can evoke physiological responses. Adrenergic modulators described herein activate one or both of the $\alpha_{2B}$ and/or $\alpha_{2C}$ receptors and have useful therapeutic actions.

The following structures are contemplated according to the present description.

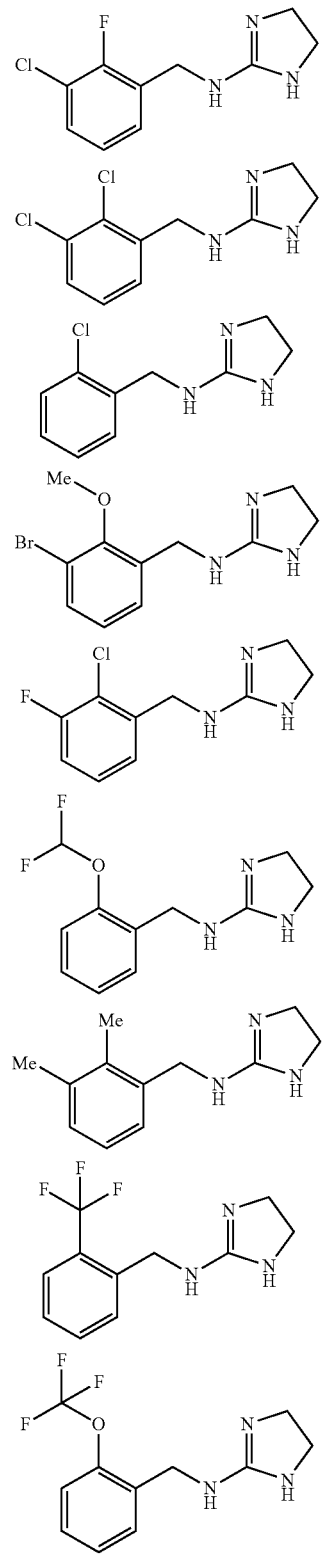

-continued

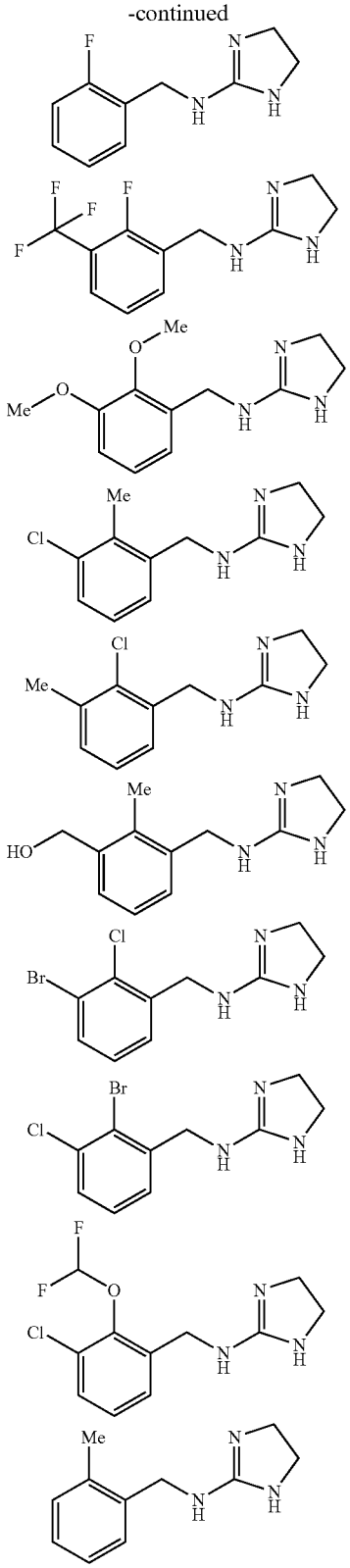

The compounds described herein may be useful for the treatment of a wide range of conditions and diseases that are alleviated by $\alpha_{2B}$ and/or $\alpha_{2C}$ activation including, but not limited to, hypertension, congestive heart failure, asthma, depression, glaucoma, elevated intraocular pressure, ischemic neuropathies, optic neuropathy, pain, visceral pain, corneal pain, headache pain, migraine, cancer pain, back pain, irritable bowel syndrome pain, muscle pain, pain associated with diabetic neuropathy, the treatment of diabetic retinopathy, other retinal degenerative conditions, stroke, cognitive deficits, neuropsychiatric conditions, drug dependence, drug addiction, withdrawal symptoms, obsessive compulsive disorder, obesity, insulin resistance, stress related conditions, diarrhea, diuresis, nasal congestions, spasticity, attention deficit disorder, psychoses, anxiety, autoimmune disease, Crohn's disease, gastritis, Alzheimer's disease, Parkinson's disease, amyotrophic lateral sclerosis, and other neurodegenerative diseases.

Applicants have discovered that these compounds activate or modulate $\alpha_{2B}$ and $\alpha_{2C}$ receptors. Additionally, these compounds act as a highly effective analgesic, particularly in chronic pain models, with minimal undesirable side effects, such as sedation and cardiovascular depression, commonly seen with agonists of $\alpha_{2B}$ and $\alpha_{2C}$ receptors.

Such compounds may be administered at pharmaceutically effective dosages. Such dosages are normally the minimum dose necessary to achieve the desired therapeutic effect; in the treatment of chronic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds may be useful in the treatment of pain in a mammal, particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without limitation, transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

Another embodiment is drawn to therapeutic compositions comprising the compounds of Formula 1, pharmaceutically acceptable derivatives, salts, prodrugs and/or combinations of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

Another embodiment is directed to methods for the treatment of pain, particularly chronic pain, through the administration of a compound of Formula 1, and pharmaceutically acceptable salts, and derivatives thereof to a mammal in need thereof. As indicated above, the compound will usually be formulated in a form consistent with the desired mode of delivery.

Some embodiments provide methods that rely on administration of one or more pharmaceutical compositions to a subject. As used herein, the term "subject" means any animal capable of experiencing pain, for example, a human or other mammal such as a primate, horse, cow, dog or cat.

The methods described herein are used to treat acute, neuropathic and chronic pain, and, as non-limiting examples, pain which is neuropathic, visceral or inflammatory in origin. In particular embodiments, the methods of the invention are used to treat neuropathic pain; visceral pain; post-operative pain; pain resulting from cancer or cancer treatment; and inflammatory pain.

Both acute and chronic pain can be treated by the methods described herein, and the term "pain" encompasses acute, neuropathic and chronic pain. As used herein, the term "acute pain" means immediate, generally high threshold, pain brought about by injury such as a cut, crush, burn, or by chemical stimulation such as that experienced upon exposure to capsaicin, the active ingredient in chili peppers. The term "chronic pain," as used herein, means pain other than acute pain and includes, without limitation, neuropathic pain, visceral pain, inflammatory pain, headache pain, muscle pain and referred pain. It is understood that chronic pain is of relatively long duration, for example, several years and can be continuous or intermittent.

Unless otherwise indicated, reference to a compound should be construed broadly to include compounds, pharmaceutically acceptable salts, prodrugs, tautomers, alternate solid forms, non-covalent complexes, and combinations thereof, of a chemical entity of a depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counterions. Salts can form from or incorporate one or more deprotonated acidic groups (e.g. carboxylic acid/carboxylate), one or more protonated basic groups (e.g. amine/ammonium), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion. Not intended to be limited by the above described compounds, various tautomers of the above compounds may be possible. For example, not intended as a limitation, tautomers are possible between the 4,5-dihydrooxazole and the adjacent nitrogen as shown below.

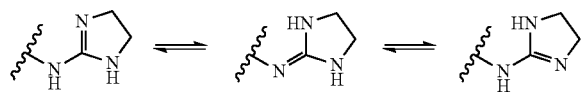 [SMILES: *NC1=NCCN1 ; *N=C1NCCN1 ; *NC1=NCCN1]

Other tautomers are possible when the compound includes, for example but not limited to, enol, keto, lactamin, amide, imidic acid, amine, and imine groups. Tautomers will generally reach an equilibrium state wherein the double bond is resonantly shared between the two bond lengths.

Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

The following examples provide synthesis methods for forming compounds described herein. One skilled in the art will appreciate that these examples can enable a skilled artisan to synthesize the compounds described herein.

Example 1

Generic Reaction 1

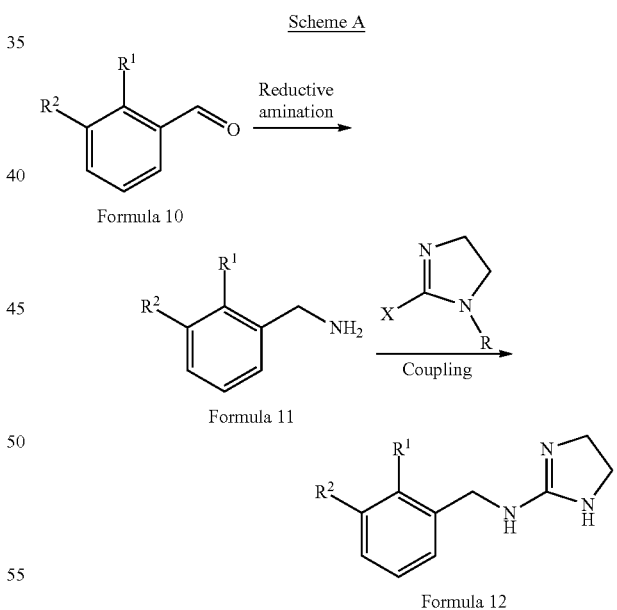

In scheme A above, Formula 11 was either commercially available or synthesized by different reductive amination methods from Formula 10. One of those methods was published by David J. H. et al (J. Org. Chem. 48: 289-294 (1983)). The key step was the coupling for Formula 11 with imidazoline which had an appropriate leaving group on the second position to give Formula 12. The leaving group may be methylthiol (R=(O)COMe) or sulfuric acid (R=H). There are also other known coupling procedures known by those skilled in the art or by modifications of known procedures known by those skilled in the art.

Scheme B

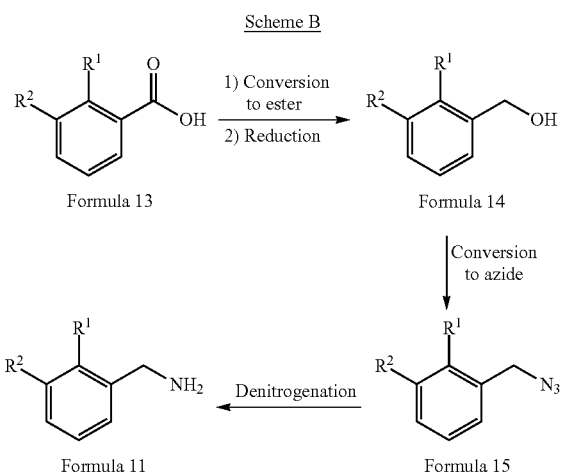

In Scheme B, another method is depicted to synthesize Formula 11 from substituted benzoic acid, substituted ester or substituted benzyl alcohol, all of which are commercially available. Formula 13 was converted to an ester which can be reduced to Formula 14 with lithium aluminum hydride (LAH) or borane as reagents. Conversion of the alcohol, Formula 14, to the azide, Formula 15, may be accomplished by methods such as Mitsunobu reaction with diphenylphosphoryl azide in one step, or converting alcohol to a good leaving group which can be replaced with azide anion. Denitrogenation of azide to amine was carried out with a phosphine such as triphenyl phosphine. Subsequent basic hydrolysis liberated the intermediate to amine.

The compounds described herein may also be synthesized by other methods known by those skilled in the art.

Example 2

Synthesis of N-(2-chloro-3-fluoro-benzyl)-4,5-dihydro-1H-imidazol-2-amine

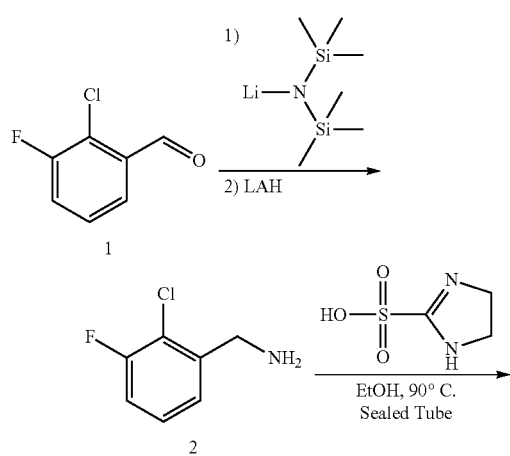

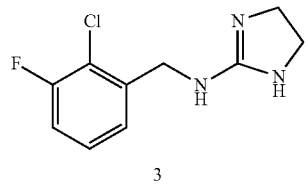

To a 7.08 mmol solution of 2-chloro-3-fluorobenzaldehyde 1 (1.00 g, commercially available from 3B Medical Systems, Inc.) in 8.0 mL of tetrahydrofuran (THF) was added 8.50 mL of 1.0M lithium bis(trimethylsilyl)-amide via syringe at 0° C. The resulting solution was stirred at 0° C. for 3 hours. 8.50 mL of 1.0M LAH was added via syringe. Three hours later, the reaction mixture was carefully poured onto crushed ice. Ammonium chloride (aq) and Rochelle's salt (aq) were added to this mixture. The aqueous layer was extracted three times with 200 mL of chloroform/isopropanol (3:1). The pooled organic layer was dried over magnesium sulfate. The mixture was filtered, and the solvents were removed under vacuum to give (2-chloro-3-fluorophenyl) methanamine 2. The weight of the product was 0.92 g.

A mixture of 0.92 g of (2-chloro-3-fluorophenyl)methanamine 2 and 0.790 g of 4,5-dihydro-1H-imidazole-2-sulfonic acid (commercially available from Astatech) in 10.0 mL of ethanol was heated in a sealed tube to 90° C. for 16 hours. Then, the reaction mixture was cooled to room temperature. Next, the ethanol was removed under vacuum. The remaining residue was basified with aqueous sodium bicarbonate solution and the pH was adjusted to about 10 with 2M sodium hydroxide. The aqueous layer was extracted three times with 100 mL of chloroform/isopropanol (3:1) The pooled organic layer was dried over magnesium sulfate and the mixture was then filtered. Amino-modified silica gel was added to the filtrate and the solvents were removed under vacuum. Purification by chromatography on amino-modified silica gel (3.5% methanol in dichloromethane) afforded 0.575 g of N-(2-chloro-3-fluoro-benzyl)-4,5-dihydro-1H-imidazol-2-amine 3 as a yellow solid.

$^1$H NMR (300 MHz, CD$_3$OD): δ=7.32-7.21 (m, 2H), 7.15-7.09 (m, 1H), 4.42 (s, 2H), 3.48 (s, 4H).

The following compounds can also be prepared according to Example 2.

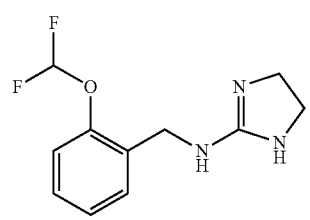 [SMILES: FC(F)Oc1ccccc1CNC1=NCCN1]

N-(2-difluoromethoxy-benzyl)-4,5-dihydro-1H-imidazol-2-amine: $^1$H NMR (300 MHz, CD$_3$OD): δ=7.43-7.32 (m, 2H), 7.24-7.16 (m, 2H), 6.90 (t, J=73.8 Hz, 1H), 4.43 (s, 2H), 3.62 (s, 4H).

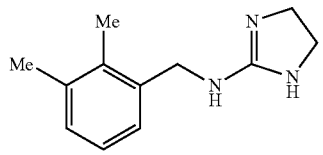 [SMILES: Cc1cccc(CNC2=NCCN2)c1C]

N-(2,3-dimethyl-benzyl)-4,5-dihydro-1H-imidazol-2-amine: $^1$H NMR (300 MHz, CD$_3$OD): δ=7.11-7.04 (m, 3H), 4.33 (s, 2H), 3.56 (s, 4H).

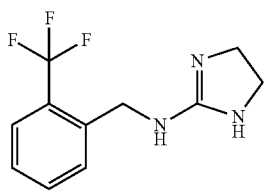 [SMILES: FC(F)(F)c1ccccc1CNC1=NCCN1]

N-(trifluoromethyl-benzyl)-4,5-dihydro-1H-imidazol-2-amine: $^1$H NMR (300 MHz, CD$_3$OD): δ=7.76-7.65 (m, 2H), 7.58-7.50 (m, 2H), 4.61 (s, 2H), 3.74 (s, 4H).

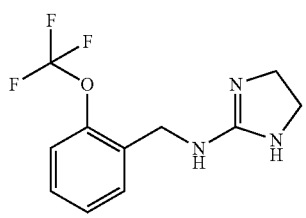 [SMILES: FC(F)(F)Oc1ccccc1CNC1=NCCN1]

N-(trifluoromethoxy-benzyl)-4,5-dihydro-1H-imidazol-2-amine: $^1$H NMR (300 MHz, CD$_3$OD): δ=7.51-7.48 (m, 1H), 7.39-7.28 (m, 3H), 4.45 (s, 2H), 3.60 (s, 4H).

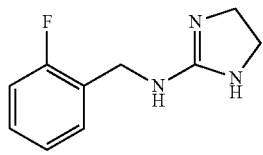

N-(2-fluoro-benzyl)-4,5-dihydro-1H-imidazol-2-amine: $^1$H NMR (300 MHz, CD$_3$OD): δ=7.40 (t, J=7.5 Hz, 1H), 7.28 (q, J=7.2 Hz, 1H), 7.11-7.03 (m, 2H), 4.41 (s, 2H), 3.56 (s, 4H).

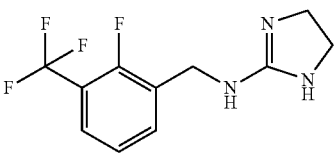 [SMILES: Fc1c(CNC2=NCCN2)cccc1C(F)(F)F]

N-(2-fluoro-3-trifluoromethyl-benzyl)-4,5-dihydro-1H-imidazol-2-amine: $^1$H NMR (300 MHz, CD$_3$OD): δ=7.66 (t, J=7.5 Hz, 1H), 7.57 (q, J=7.5 Hz, 1H), 7.30 (t, J=7.5 Hz, 1H), 4.42 (s, 2H), 3.50 (s, 4H).

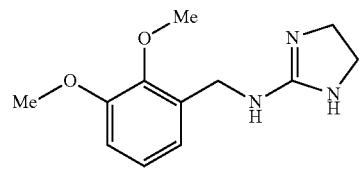 [SMILES: COc1cccc(CNC2=NCCN2)c1OC]

N-(2,3-dimethoxy-benzyl)-4,5-dihydro-1H-imidazol-2-amine: $^1$H NMR (300 MHz, CD$_3$OD): δ=7.05-6.87 (m, 3H), 4.34 (s, 2H), 3.83 (s, 6H), 3.55 (s, 4H).

Example 3

Synthesis of N-(3-bromo-2-methoxy-benzyl)-4,5-dihydro-1H-imidazol-2-amine

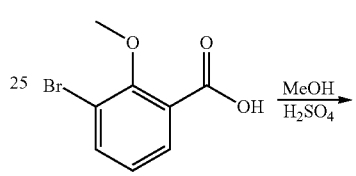

4

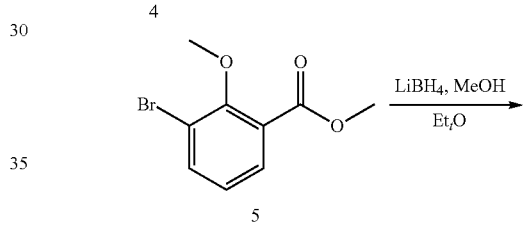

5

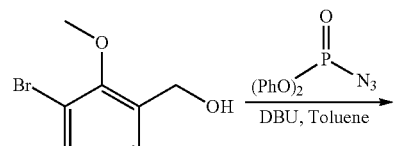

6

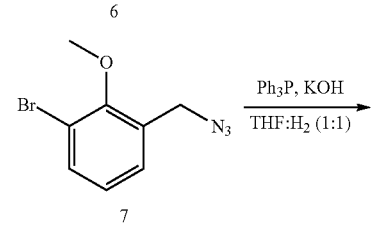

7

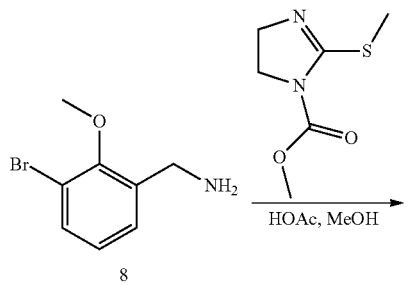

8

-continued

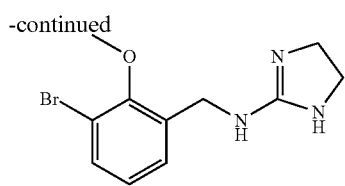

9

5.0 mL of sulfuric acid (H$_2$SO$_4$) was slowly added to a solution of 5.0 g of 3-bromo-2-methoxy-benzoic acid 4 in 100 mL of methanol (MeOH). The resulting solution was heated to reflux overnight. The solution was cooled to room temperature and quenched with sodium bicarbonate to pH 7. The aqueous layer was extracted several times with ethyl acetate. The combined organic extracts were washed with brine and dried over sodium sulphate. The resulting mixture was filtered. The solvents were evaporated under reduced pressure to afford 5.3 g of 3-bromo-2-methoxy-benzoic acid methyl ester 5.

2.4 g of lithium borohydride (LiBH$_4$) was added to a solution of 5.3 g of 3-bromo-2-methoxy-benzoic acid methyl ester 5 in 200 mL of ether (Et$_2$O) at 0° C. After stirring for 5 minutes, 5 mL of methanol was added. The reaction mixture was warmed to room temperature and kept there for 2.5 hours. Thereafter, 2.4 g more of lithium borohydride was added. The reaction mixture was quenched with aluminum chloride. After standard aqueous work up, and silica gel column purification (hexane/ethyl acetate 2:1), 4.0 g of 3-bromo-2-methoxy-phenyl-methanol 6 was obtained.

6.00 g of diphenyl phosphorazidate and 4.1 g of 1,8-diazabicyclo[5.4.0] undec-7-ene were added to 4.0 g of 3-bromo-2-methoxy-phenyl-methanol 6 in 100 mL of toluene at 0° C. The mixture was stirred at room temperature overnight. The reaction mixture was quenched with aqueous ammonium chloride. The aqueous layer was extracted with ethyl acetate/THF. The pooled organic extracts were washed with brine and dried over magnesium sulfate. The mixture was filtered. The solvents were removed under vacuum. The residue was purified by chromatography on silica gel to give 1-azidomethyl-3-bromo-2-methoxy-benzene 7.

1.1 g of potassium hydroxide (KOH) and 5.8 g of triphenyl phosphine (Ph$_3$P) were added to a solution of 1-azidomethyl-3-bromo-2-methoxy-benzene 7 in 100 mL of THF and 10 mL of water. The mixture was stirred overnight at room temperature. The mixture was quenched with aqueous concentrated hydrochloride. After standard acid/base aqueous work up, 3.9 g of crude 3-bromo-2-methoxy-benzylamine 8 was obtained (after two steps).

10 mL of acetic acid (HOAc) was added to a solution of 3.9 g of 3-bromo-2-methoxy-benzylamine 8 and 3.1 g of methyl 2-(methylthio)-4,5-dihydro-1H-imidazole-1-carboxylate in 100 mL of methanol. The resulting solution was heated to a gentle reflux and refluxed overnight. The solution was cooled to room temperature, quenched with sodium hydroxide and extracted with ethyl acetate. The combined organic extracts were washed with brine and dried over magnesium sulfate. The mixture was then filtered. The solvents were removed under vacuum. The remaining residue was purified by chromatography on silica gel (10% saturated ammonia methanol in dichloromethane) to give (3-bromo-2-methoxy-benzyl-4,5-dihydro-1H-imidazol-2-yl)-amine 9.

$^1$H NMR (300 MHz, CD$_3$OD): δ=7.51 (d, J=3 Hz, 1H), 7.25-7.29 (m, 1H), 6.80 (d, J=9 Hz, 1H), 4.46 (s, 2H), 3.84 (s, 4H), 3.63 (s, 3H).

The following compounds can also be prepared according to Example 3.

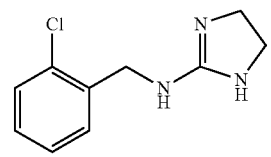 [SMILES: Clc1ccccc1CNC1=NCCN1]

N-(2-chloro-benzyl)-4,5-dihydro-1H-imidazol-2-amine: $^1$H NMR (300 MHz, CD$_3$OD): δ=7.51-7.53 (m, 1H), 7.28-7.29 (m, 1H), 7.14-7.21 (m, 2H), 4.59 (s, 2H), 3.58 (s, 4H).

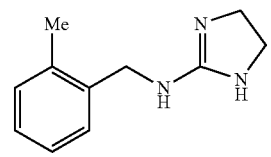

N-(2-methyl-benzyl)-4,5-dihydro-1H-imidazol-2-amine: $^1$H NMR (300 MHz, CD$_3$OD): δ=7.08-7.12 (m, 4H), 4.45 (d, J=6 Hz, 2H), 3.54 (s, 4H), 2.28 (s, 3H).

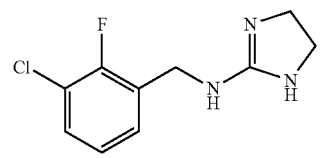

N-(3-chloro-2-fluoro-benzyl)-4,5-dihydro-1H-imidazol-2-amine: $^1$H NMR (300 MHz, CD$_3$OD): δ=7.40-7.31 (m, 2H), 7.16-67.10 (m, 1H), 4.42 (s, 2H), 3.56 (s, 4H).

Example 4

Synthesis of N-(2,3-dichlorobenzyl)-4,5-dihydro-1H-imidazol-2-amine

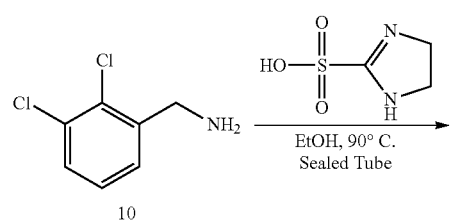

A mixture of 5.32 g of (2,3-dichlorophenyl)methanamine 10 and 4.56 g of 4,5-dihydro-1H-imidazole-2-sulfonic acid are mixed in 40.0 mL ethanol (EtOH) and heated in a sealed tube at 90° C. for 16 hours. Then, the reaction mixture was cooled to room temperature. Next, the ethanol was removed under vacuum. The remaining residue was basified with aqueous sodium bicarbonate solution and the pH was adjusted to about 10 with 2M sodium hydroxide. The aqueous layer was extracted three times with 400 mL of chloroform/isopropanol (3:1). The pooled organic layer was dried over magnesium sulfate and the mixture was then filtered. The filtrate was added to amino-modified silica gel (4-5% methanol in dichloromethane) and afforded 3.99 g of Compound 11 as a yellow solid.

$^1$H NMR (300 MHz, CD$_3$OD): δ=7.43 (dd, J=7.8, 1.8 Hz, 1H), 7.37-7.33 m, 1H), 7.26 (t, J=7.8 Hz, 1H), 4.43 (s, 2H), 3.51 (s, 4H).

Example 5

Biological Intrinsic Activity Data

Certain compounds described herein were tested for α-adrenergic activity using the Receptor Selection and Amplification Technology (RSAT) assay (Messier et al., 1995, Pharmacol. Toxicol. 76, pp. 308-311). Cells expressing each of the α$_2$ adrenergic receptors alone were incubated with the various compounds and a receptor-mediated growth response was measured. The compound's activity is expressed as its relative efficacy compared to standard full agonist (see Table 1 below). The compounds described herein activate α$_{2B}$ and/or α$_{2C}$ receptors.

| Compound | α$_{1A}$ | α$_{2B}$ | α$_{2C}$ |
|---|---|---|---|
| (F, Cl benzyl imidazoline) | 587 (1.01) | 33 (1.11) | 484 (0.60) |
| (Cl benzyl imidazoline) | 345 (1.12) | 50 (0.81) | 471 (0.86) |
| (Me benzyl imidazoline) | 430 (0.79) | 56 (0.92) | 1594 (0.63) |
| (Me-O, Br benzyl imidazoline) | nd | 499 (0.73) | nd |
| (Cl, Cl benzyl imidazoline) | 282 (1.10) | 14.0 (0.94) | 46.8 (0.48) | nd = not determined

Example 6

Biological Intrinsic Activity Data

Various concentrations of N-(2,3-dichlorobenzyl)-4,5-dihydro-1H-imidazol-2-amine were administered orally to Chung model rats. A model in accordance with *Kim and Chung* 1992, Pain 150, pp 355-363 (*Chung* model), for chronic pain (in particular peripheral neuropathy) involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Rats are anesthetized before surgery. The surgical site is shaved and prepared either with betadine or Novocain. Incision is made from the thoracic vertebra XIII down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

A complete hemostasis is confirmed, then the wounds are sutured. A small amount of antibiotic ointment is applied to the incised area, and the rat is transferred to the recovery plastic cage under a regulated heat-temperature lamp. On the day of the experiment, at least seven days after the surgery, typically six rats per test group are administered the test drugs by intraperitoneal (i.p.) injection or oral gavage. For i.p. injection, the compounds are formulated in d H$_2$O and given in a volume of 1 ml/kg body weight using an 18-gauge, 3 inch gavage needle that is slowly inserted through the esophagus into the stomach.

Tactile allodynia is measured prior to and 30 minutes after drug administration using von Frey hairs that are a series of fine hairs with incremental differences in stiffness. Rats are placed in a plastic cage with a wire mesh bottom and allowed to acclimate for approximately 30 minutes. The von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980) hereby incorporated by reference. The post-drug threshold is compared to the pre-drug threshold and the percent reversal of tactile sensitivity is calculated based on a normal threshold of 15.1 grams.

Table 2 below shows the peak allodynia reversal at 30 µg/kg, 100 µg/kg or 300 µg/kg doses.

TABLE 2

| Dose | Peak Allodynia Reversal (Oral, 30 min.) |
|---|---|
| 300 µg/kg | 84% +/− 7.5% |
| 100 µg/kg | 68% +/− 12.7% |
| 30 µg/kg | 28% +/− 9.5% |

As shown in Table 2, 30 µg/kg oral dosage resulted in 28% allodynia reversal. The analgesic effect was seen quickly, in about 30 minutes. FIG. 1 shows a peak percent allodynia reversal at 30 minutes followed by a steady decrease to baseline at about 120 minutes.

Example 7

In Vivo Activity Data

Data was acquired from wild type rats administered N-(2,3-dichlorobenzyl)-4,5-dihydro-1H-imidazol-2-amine intraperitoneally (IP). Rats were split into groups of six and administered 1 mg/kg or 10 mg/kg doses of N-(2,3-dichlorobenzyl)-4,5-dihydro-1H-imidazol-2-amine to assess the sedative effects of the administration of the agent. As can be seen in both FIG. 2 and Table 3, 10 mg/kg had a significant sedative effect on the dosed rats.

TABLE 3

| Dose | Sedative Effect (IP) |
|---|---|
| 1 mg/kg | No significant effect |
| 10 mg/kg | 23% sedating |

Example 8

Dideoxycytidine (ddC) Model

The ddC Model in the rat is a relatively new model of neuropathic pain discovered from clinical treatment of the AIDS virus. Patients taking dideoxycytidine (ddC) for AIDS Highly Active Antiretroviral Therapy (HAART) reported development of painful neuropathies. The experimental animal model in the rat for neuropathic pain by ddC injection manifests symptoms of human patients with causalgia. It is considered predictive of clinical activity against neuropathic pain (Joseph et al, 2004). Compound N-(2,3-dichlorobenzyl)-4,5-dihydro-1H-imidazol-2-amine was tested in this ddC model of allodynic pain. The compound was administered intraperitoneally to male ddC treated rats.

The animals are injected intraperitoneally (IP) with 25 mg/kg dideoxycytidine (ddC) using a sterile 30 gauge needle. Approximately 3 weeks after the ddC injection a painful neuropathy develops causing sensitivity to light touch on the animals' extremities. This neuropathy can last for 2-3 months. The animals show no spontaneous pain, only a heightened response to mechanical stimuli (von Frey hair stimulation). The allodynia is quantitated in the animals receiving ddC injections by stimulation with a series of 8 Von Frey hairs on the mid planter area of the hind paws in the up-down manner described by Dixon (Dixon, 1980).

Male Sprague-Dawley rats (Charles River, Wilmington, Mass.) weighing approximately 150-300 grams were used for these studies. All experimental animals received N-(2,3-dichlorobenzyl)-4,5-dihydro-1H-imidazol-2-amine or vehicle in a single acute IP dose. In all studies, baseline measurements were taken prior to drug administration and then at 15, 30, 60 and 120 minutes post acute IP dosing (vehicle or N-(2,3-dichlorobenzyl)-4,5-dihydro-1H-imidazol-2-amine). The % allodynia reversal is calculated as: [(Postdrug threshold—Predrug threshold)/(15-Predrug threshold)]×100.

N-(2,3-dichlorobenzyl)-4,5-dihydro-1H-imidazol-2-amine was dissolved in 42% DMSO (dimethyl sulfoxide; Sigma, St. Louis, Mo.) at a concentration of 3 mg/ml. This stock solution was kept frozen at −20° C., was thawed on the day of the study and diluted in dd-$H_2O$ to concentrations ranging from 0.01-0.1 mg/ml for IP dosing (dosing volume=1 ml/kg). The vehicle is dd-$H_2O$ for these studies.

Data were compiled and analyzed using Microsoft Excel and/or Kaleidagraph. Data are expressed as mean± standard error of the mean. Comparisons between drug treated and vehicle groups were made using a two-tailed, 2-sample, unpaired t-test. Comparisons between baselines (pre-drug) and post-drug time points were made using a two-tailed, 2-sample, paired t-test.

the ddC Model in male rats in a dose-related manner. A maximal effect of 86% allodynia reversal was measured at 30 minutes post 0.1 mg/kg IP N-(2,3-dichlorobenzyl)-4,5-dihydro-1H-imidazol-2-amine administration. The minimal statistically significant efficacious dose was 0.03 mg/kg, resulting in a 67% allodynia reversal (Table 4). The no-effect dose was 0.01 mg/kg.

N-(2,3-dichlorobenzyl)-4,5-dihydro-1H-imidazol-2-amine alleviates the allodynia in

TABLE 4

Acute IP N-(2,3-dichlorobenzyl)-4,5-dihydro-1H-imidazol-2-amine Administration in the ddC Model of Neuropathic Pain.

| | % Allodynia Reversal: 15 min post dose | % Allodynia Reversal: 30 min post dose | % Allodynia Reversal: 60 min post dose | % Allodynia Reversal: 120 min post dose |
|---|---|---|---|---|
| 1 ml/kg vehicle IP | 1.1 ± 1.6 | 0.7 ± 0.8 | 1.2 ± 1.3 | 1.5 ± 1.8 |
| 0.01 mg/kg 200762 IP | 1.8 ± 1.6 | 3.0 ± 1.7 | 1.5 ± 2.0 | 0.1 ± 1.3 |
| 0.03 mg/kg 200762 IP | 34 ± 3.9** | 67 ± 9.0** | 20 ± 3.7** | 2.0 ± 2.6 |
| 0.1 mg/kg 200762 IP | 58 ± 9.1** | 86 ± 6.3** | 34 ± 2.5** | 0.9 ± 1.2 |

Data is expressed as mean % MPE, which represents the % allodynia reversal, ± standard error of the mean. n = 6 in all groups.
Significance values relative to vehicle: *p < 0.05; **p < 0.01.

N-(2,3-dichlorobenzyl)-4,5-dihydro-1H-imidazol-2-amine alleviates the allodynia in male ddC treated rats. The antiallodynic effect peaks at 0.1 mg/kg IP resulting in a 86% reduction of allodynia at 30 minutes post IP dose.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of treating Crohn's disease in a mammal, the method comprising administering to the mammal in need of such treatment a pharmaceutically effective dose of N-(2,3-dichlorobenzyl)-4,5-dihydro-1H-imidazol-2-amine having the following structure:

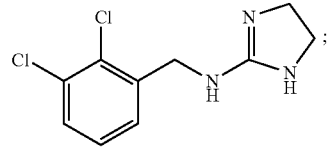 [SMILES: Clc1cccc(CNC2=NCCN2)c1Cl]

or a pharmaceutically acceptable salt thereof.

2. The method of claim 1, wherein the dose is administered by an oral route.

3. The method of claim 2, wherein the dose is orally administered in the form of a tablet, liquid, capsule or powder.

4. The method of claim 1, wherein the dose is administered by a transdermal, parenteral, subcutaneous, intranasal, intrathecal, intramuscular, intravenous or intrarectal route.

5. The method of claim 1, wherein the mammal is a human.

* * * * *

UNITED STATES PATENT AND TRADEMARK OFFICE
CERTIFICATE OF CORRECTION

PATENT NO.       : 9,849,113 B2
APPLICATION NO.  : 15/446650
DATED            : December 26, 2017
INVENTOR(S)      : Daniel W. Gil et al.

It is certified that error appears in the above-identified patent and that said Letters Patent is hereby corrected as shown below:

On the Title Page

In item (54), Line 1, delete "α" and insert -- ALPHA --, therefor.

In item (56), in Column 2, under "Other Publications", Line 19, delete "497-904," and insert -- 497-504, --, therefor.

On the page 2, in item (56), in Column 1, under "Other Publications", Line 2, delete "Alfa-1 and Alfa-" and insert -- Alpha-1 and Alpha- --, therefor.

In the Drawings

On sheet 1 of 3, in Figure 1, Line 5, delete "ug/kg" and insert -- µg/kg --, therefor.

On sheet 1 of 3, in Figure 1, Line 7, delete "ug/kg" and insert -- µg/kg --, therefor.

On sheet 1 of 3, in Figure 1, Line 9, delete "ug/kg" and insert -- µg/kg --, therefor.

Figure 2:
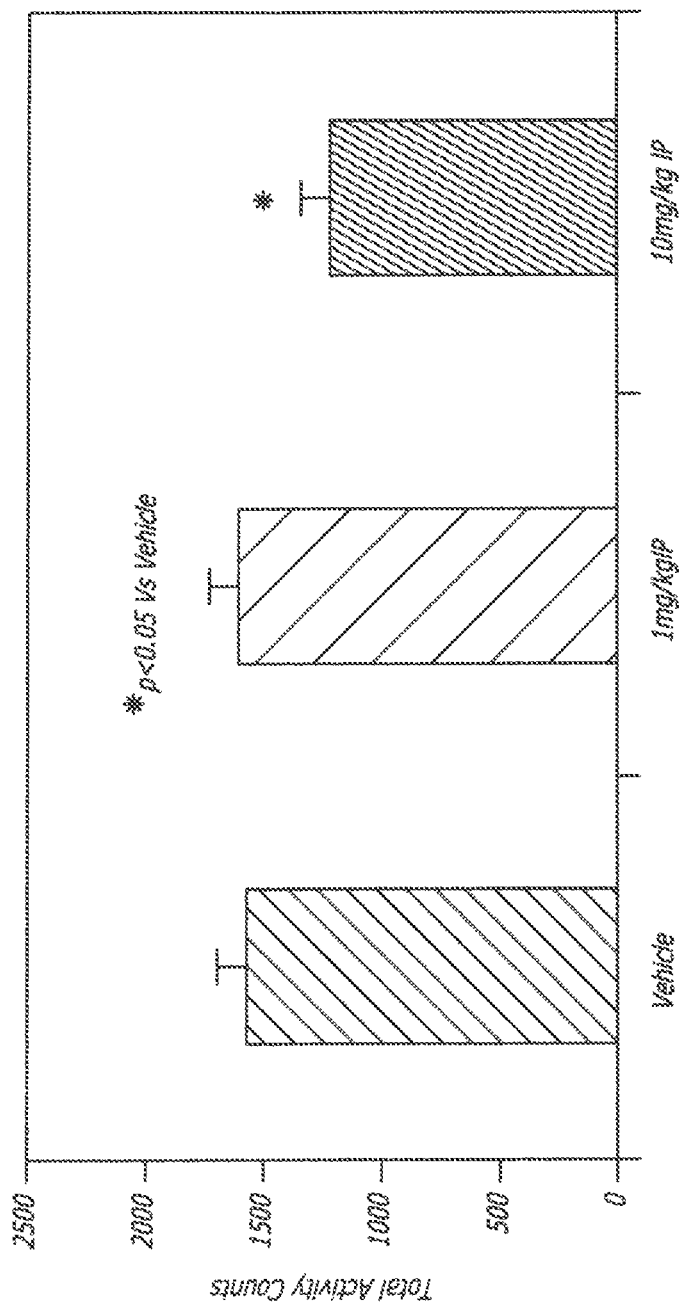
FIG. 2 depicts sedative effects (total activity counts) 30 minutes post intraperitoneal injection of 1 mg/kg and 10 mg/kg doses of N-(2,3-dichlorobenzyl)-4,5-dihydro-1H-imidazol-2-amine.

On sheet 2 of 3, in Figure 2, Line 7, delete "1mg/kgIP" and insert -- 1mg/kg IP --, therefor.

Figure 3:
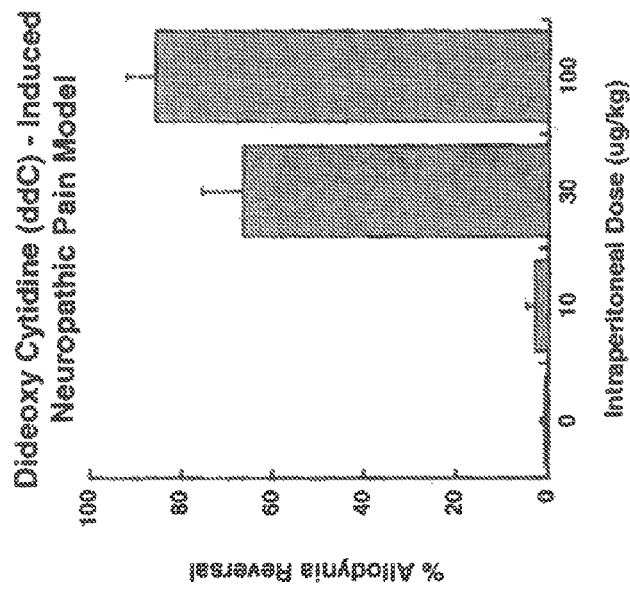
FIG. 3 shows compound N-(2,3-dichlorobenzyl)-4,5-dihydro-1H-imidazol-2-amine activity in the Drug-Induced Neuropathic Pain Model 30 minutes after a single intraperitoneal dose at concentrations of 10 μg/kg, 30 μg/kg or 100 μg/kg.

On sheet 3 of 3, in Figure 3, Line 12, delete "(ug/kg)" and insert -- (µg/kg) --, therefor.

In the Specification

In Column 1, Line 1, delete "α" and insert -- ALPHA --, therefor.

In Column 5, Line 28, delete "indans" and insert -- indanes --, therefor.

In Column 5, Line 51, delete "$C_{1-10}$alkynyl," and insert -- $C_{1-10}$ alkynyl, --, therefor.

Signed and Sealed this
Eighth Day of May, 2018

Andrei Iancu
*Director of the United States Patent and Trademark Office*

CERTIFICATE OF CORRECTION (continued)
U.S. Pat. No. 9,849,113 B2

In Column 6, Line 66, delete "alkenyl." and insert -- alkenyl, --, therefor.

In Column 14, Line 38, after "(3:1)" insert -- . --.

In Column 16, Lines 32-33, delete " $\xrightarrow{\text{LiBH}_4, \text{MeOH}}_{\text{Et}O}$ " and insert -- $\xrightarrow{\text{LiBH}_4, \text{MeOH}}_{\text{Et}_2\text{O}}$ --, therefor.

In Column 16, Line 50, delete "THF:H$_2$" and insert -- THF:H$_2$O --, therefor.

In Column 17, Line 35, delete "] undec" and insert -- ]undec --, therefor.

In Column 22, Line 18, delete "mean±" and insert -- mean ± --, therefor.

In Column 22, Line 24, delete "the" and insert -- The --, therefor.